(12) United States Patent
Steidl et al.

(10) Patent No.: US 11,137,397 B2
(45) Date of Patent: Oct. 5, 2021

(54) PEPTIDES FOR BLOCKING IL1RAP PROTEIN-PROTEIN INTERACTION AND USES THEREOF FOR TREATMENT OF DISEASE

(71) Applicant: Albert Einstein College of Medicine, Bronx, NY (US)

(72) Inventors: Ulrich Steidl, New Rochelle, NY (US); Laura Barreyro De Pujato, Bronx, NY (US); Mario Pujato, Bronx, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 638 days.

(21) Appl. No.: 15/524,363

(22) PCT Filed: Nov. 23, 2015

(86) PCT No.: PCT/US2015/062060
§ 371 (c)(1),
(2) Date: May 4, 2017

(87) PCT Pub. No.: WO2016/085832
PCT Pub. Date: Jun. 2, 2016

(65) Prior Publication Data
US 2018/0275123 A1 Sep. 27, 2018

Related U.S. Application Data

(60) Provisional application No. 62/083,417, filed on Nov. 24, 2014.

(51) Int. Cl.
| | | |
|---|---|---|
| *A61K 38/00* | (2006.01) | |
| *G01N 33/566* | (2006.01) | |
| *C07K 14/00* | (2006.01) | |
| *A61P 35/00* | (2006.01) | |
| *C07K 14/47* | (2006.01) | |
| *C07K 14/545* | (2006.01) | |
| *C07K 14/715* | (2006.01) | |

(52) U.S. Cl.
CPC ............ *G01N 33/566* (2013.01); *A61P 35/00* (2018.01); *C07K 14/001* (2013.01); *C07K 14/4702* (2013.01); *C07K 14/545* (2013.01); *C07K 14/7155* (2013.01); *A61K 38/00* (2013.01); *G01N 2333/545* (2013.01); *G01N 2333/7155* (2013.01); *G01N 2500/02* (2013.01)

(58) Field of Classification Search
CPC .............. C07K 14/001; C07K 14/4702; C07K 14/545; C07K 14/7155; A61P 35/00; A61P 35/02; A61K 38/00
See application file for complete search history.

(56) References Cited

U.S. PATENT DOCUMENTS

| | | |
|---|---|---|
| 2006/0094663 A1 | 5/2006 | Chemtob et al. |
| 2014/0017167 A1 | 1/2014 | Fioretos et al. |
| 2014/0187604 A1 | 7/2014 | Steidl et al. |
| 2014/0255431 A1 | 9/2014 | Majeti et al. |
| 2015/0147271 A1 | 5/2015 | Steidl et al. |
| 2015/0299336 A1 | 10/2015 | Steidl |
| 2015/0329643 A1 | 11/2015 | Steidl et al. |
| 2015/0359815 A1 | 12/2015 | Steidl et al. |
| 2016/0340737 A1 | 11/2016 | Steidl et al. |

FOREIGN PATENT DOCUMENTS

WO  WO2011/021014  *  2/2011

OTHER PUBLICATIONS

Askmyr, M. et al. Selective killing of candidate AML stem cells by antibody targeting of IL1RAP. Blood, 2013, 121(18):3709-3713.*
Barreyro, L, et al. Overexpression of IL-1 receptor accessory protein in stem and progenitor cells and oudtcome correlation in AML and MDS. Blood, 2012, 120(6): 1290-1298.*
Dinarello, C.A. Biolologic basis for interleukin-1 in disease. Blood, 1996, 87(6):2095-2147.*
Dinarello, C.A. et al. Treating inflammation by blocking interleukin-1 in a broad spectrum of diseases. Nature Reviews Drug Discovery, 2012, 11:633-652.*
Liew, F.Y., et al. Disease-associated functions of IL-33; the new kid in the IL-1 family. Nature Reviews Immunology, 2010, 10:103-110.*
Subramaniam S., et al. The interleukin 1 receptor family. Developmental and Comparative Immunology, 2004, 28:415-428.*
EMBOSS Needle comparison of IL1R1 and IL1RL1, Nov. 8, 2019, accessed at https://www.ebi.ac.uk/Tools/psa/emboss_needle/.*
Agerstam, H., et al. Antibodies targeting human IL1RAP (IL1R3) show therapeutic effects in xenograft models of acute myeloid leukemia. Proc. Natl. Acad. Sci. USA, 2015, 112(34):10786-10791).*
Mitchell, K., et al. IL1RAP potentiates multiple oncogenic signaling pathways in AML. J. Exp. Med., 2018, 215(6):1709-1717.*
Agerstam, H., et al. IL1RAP antibodies block IL-1-induced expansion of candidate CML stem cells and mediate cell killing in xenograft models. Blood, 2016, 128(23):2683-2693.*
Ardura-Fabregat, A., et al. Targeting neuroinflammation to treat Alzheimer's disease. CNS Drugs, 2017, 1057-1082.*
Cavalli, G., et al. Anakinra therapy for non-cancer inflammatory diseases. Frontiers in Pharmacology, 2018, 9:Article 1157, p. 1-21.*
Dinarello, C.A. et al. Treating inflammation by blocking interleukin-1 in humans. Seminars in Immunology, 2013, 25:469-484.*
PCT International Search Report and Written Opinion dated Mar. 25, 2016 for PCT International Patent Application No. PCT/US2015/62060, 11 pages.
Barreyro L et al., entitled "Abstract C225: IL1RAP as functionally relevant target for stem-cell directed therapy in acute myeloid leukemia (AML) and myelodysplastic syndromes (MDS)," Mol Cancer Ther, Nov. 12, 2013; C225, 2 pages.

(Continued)

*Primary Examiner* — Prema M Mertz
(74) *Attorney, Agent, or Firm* — Fox Rothschild LLP

(57) ABSTRACT

Methods and agents are provided for inhibiting interleukin 1 receptor accessory protein (IL1RAP) protein-protein interaction to treat a broad spectrum of diseases and conditions.

4 Claims, 12 Drawing Sheets

Specification includes a Sequence Listing.

(56) References Cited

OTHER PUBLICATIONS

UniProtKB entry C7Z2X8 (Oct. 13, 2009) [retrieved on Mar. 17, 2016 from http://www.uniprot.org/uniprot/C7Z2X8, 3 pages.
UniProtKB entry V4EQS5 (Jan. 22, 2014) [retrieved on Mar. 17, 2016 from http://www.uniprot.org/uniprot/V4EQS5, 3 pages.
Lewis et al., "Interleukin-I and cancer progression: the emerging role of interleukin-I receptor antagonist as a novel therapeutic agent in cancer treatment", Journal of Translational Medicine 2006, 4:48.
Krause et al., "The role of interleukin-1 in allergy-related disorders", Curr Opin Allergy Clin Immunol 2012, 12:477-484.

* cited by examiner

```
IL1R1    ---KEREEKIILVSSANEIDVRPCPLNP--------NEGTITWYKDP----VSTEQASRI  45
IL1R2    CRFRGRHYKREFRLEGEPVALR-CPQVFYWLWASVSPRINLTWHKNDSARTVPGEEETRM  59

IL1R1    HQHKEKLWFVPAKVEDSGHYYCVVRNSSYCLRIKISAKFVENEPNLCYNAQAIFKQKLPV 105
IL1R2    WAQDGALWLLPALQEDSGTYVCTTRNASYCDKMSIELRVFEN--TDAFLPFISYPQILTL 117

IL1R1    AGDGGLVCPYMEFFKNENNELPKLQWYKDCKPLLLDNIHFSGVK--DRLIVMNVAEKHRG 163
IL1R2    STSGVLVCPDLSEFTRDKTDV-KIQWYKDSLLLDKDNEKFLSVRGTTHLLVHDVALEDAG 176

IL1R1    NYTCHASYTYLGKQYPITRVIEFITLEENKPTRPVIVSPAN-ETMEVDLQIQLICNVTG- 221
IL1R2    YYRCVLTFAHEGQQYNITRSIELRIKKKKEETIPVIISPLKTISASLGSRLTIPCKVFLG 236

IL1R1    ---QLSDIAYWKWNGSVIDEDDPVLGEDYYSVENPANKRRSTLITVLNISEIESRFYKHP 278
IL1R2    TGTPLTTMLKWTANDTHIESAYPGGRVTEGPRQEYSENNENVIEVPLIFDPVTREDLHMD 296

IL1R1    FTCFAKNTHGIDAAYIQL-- 296
IL1R2    FKCVVHNTLSFQTLRTTVKE 316
```

FIG. 2

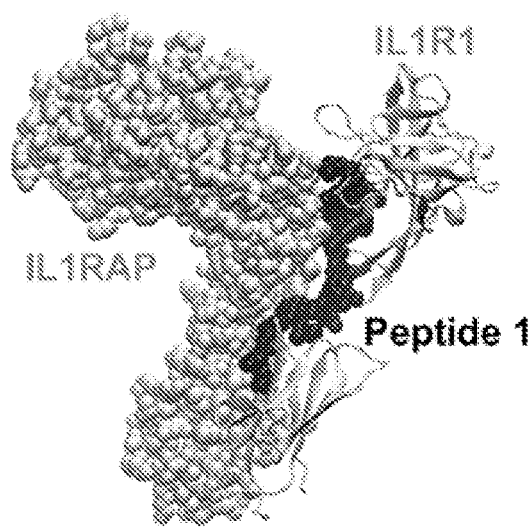
Peptide 1 (p1):
AGDKDRLIVMENKPTRPV
118   161   203
120   167   210
Peptide 2 (p2):
AGDKDRLIVMENKPTHGID
            203   301
            207   304
FIG. 3A
FIG. 3B
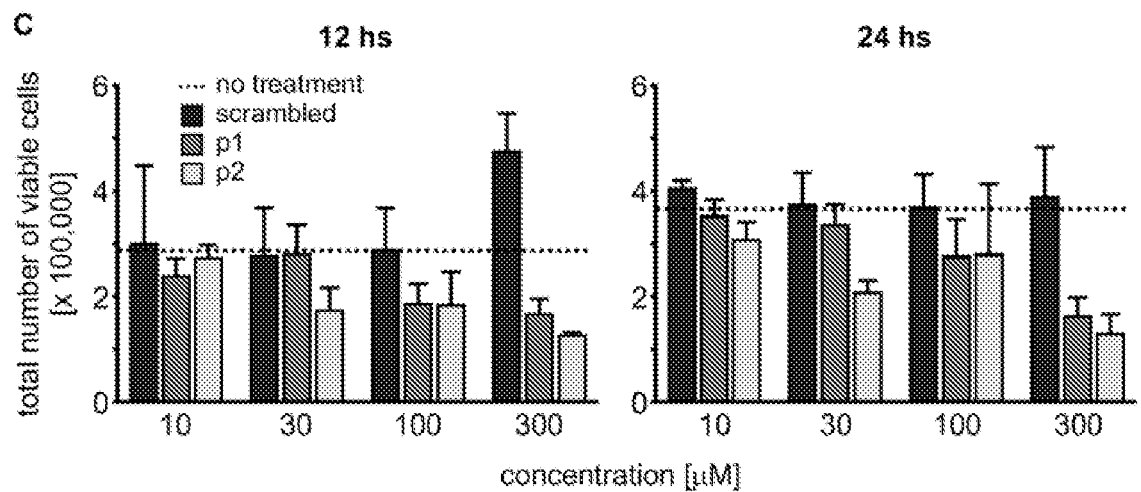
FIG. 3C

```
                           SEQUENCE LISTING

<160> NUMBER OF SEQ ID NOS: 7

<210> SEQ ID NO 1
<211> LENGTH: 18
<212> TYPE: PRT
<213> ORGANISM: Artificial Sequence
<220> FEATURE:
<223> OTHER INFORMATION: inhibits IL1RAP protein-protein interaction

<400> SEQUENCE: 1

Ala Gly Asp Lys Asp Arg Leu Ile Val Met Glu Asn Lys Pro Thr Arg
1               5                   10                  15

Pro Val

<210> SEQ ID NO 2
<211> LENGTH: 19
<212> TYPE: PRT
<213> ORGANISM: Artificial Sequence
<220> FEATURE:
<223> OTHER INFORMATION: inhibits IL1RAP protein-protein interaction

<400> SEQUENCE: 2

Ala Gly Asp Lys Asp Arg Leu Ile Val Met Glu Asn Lys Pro Thr His
1               5                   10                  15

Gly Ile Asp

<210> SEQ ID NO 3
<211> LENGTH: 18
<212> TYPE: PRT
<213> ORGANISM: Artificial Sequence
<220> FEATURE:
<223> OTHER INFORMATION: scrambled control peptide

<400> SEQUENCE: 3

Leu Lys Asp Met Pro Gly Arg Pro Asn Glu Arg Asp Lys Val Ala Ile
1               5                   10                  15

Thr Val

<210> SEQ ID NO 4
<211> LENGTH: 296
<212> TYPE: PRT
<213> ORGANISM: Homo sapiens

<400> SEQUENCE: 4
```

```
Lys Glu Arg Glu Glu Lys Ile Ile Leu Val Ser Ser Ala Asn Glu Ile
1               5                   10                  15

Asp Val Arg Pro Cys Pro Leu Asn Pro Asn Glu Gly Thr Ile Thr Trp
            20                  25                  30

Tyr Lys Asp Pro Val Ser Thr Glu Gln Ala Ser Arg Ile His Gln His
        35                  40                  45

Lys Glu Lys Leu Trp Phe Val Pro Ala Lys Val Glu Asp Ser Gly His
    50                  55                  60

Tyr Tyr Cys Val Val Arg Asn Ser Ser Tyr Cys Leu Arg Ile Lys Ile
65                  70                  75                  80

Ser Ala Lys Phe Val Glu Asn Glu Pro Asn Leu Cys Tyr Asn Ala Gln
                85                  90                  95

Ala Ile Phe Lys Gln Lys Leu Pro Val Ala Gly Asp Gly Gly Leu Val
            100                 105                 110

Cys Pro Tyr Met Glu Phe Phe Lys Asn Glu Asn Asn Glu Leu Pro Lys
            115                 120                 125

Leu Gln Trp Tyr Lys Asp Cys Lys Pro Leu Leu Asp Asn Ile His
    130                 135                 140

Phe Ser Gly Val Lys Asp Arg Leu Ile Val Met Asn Val Ala Glu Lys
145                 150                 155                 160

His Arg Gly Asn Tyr Thr Cys His Ala Ser Tyr Thr Tyr Leu Gly Lys
                165                 170                 175

Gln Tyr Pro Ile Thr Arg Val Ile Glu Phe Ile Thr Leu Glu Glu Asn
            180                 185                 190

Lys Pro Thr Arg Pro Val Ile Val Ser Pro Ala Asn Glu Thr Met Glu
            195                 200                 205

Val Asp Leu Gln Ile Gln Leu Ile Cys Asn Val Thr Gly Gln Leu Ser
    210                 215                 220

Asp Ile Ala Tyr Trp Lys Trp Asn Gly Ser Val Ile Asp Glu Asp Asp
225                 230                 235                 240

Pro Val Leu Gly Glu Asp Tyr Tyr Ser Val Glu Asn Pro Ala Asn Lys
            245                 250                 255

Arg Arg Ser Thr Leu Ile Thr Val Leu Asn Ile Ser Glu Ile Glu Ser
            260                 265                 270

Arg Phe Tyr Lys His Pro Phe Thr Cys Phe Ala Lys Asn Thr His Gly
        275                 280                 285

Ile Asp Ala Ala Tyr Ile Gln Leu
            290                 295

<210> SEQ ID NO 5
<211> LENGTH: 316
<212> TYPE: PRT
<213> ORGANISM: Homo sapiens

<400> SEQUENCE: 5

Cys Arg Phe Arg Gly Arg His Tyr Lys Arg Glu Phe Arg Leu Glu Gly
1               5                   10                  15

Glu Pro Val Ala Leu Arg Cys Pro Gln Val Pro Tyr Trp Leu Trp Ala
            20                  25                  30

Ser Val Ser Pro Arg Ile Asn Leu Thr Trp His Lys Asn Asp Ser Ala
        35                  40                  45

Arg Thr Val Pro Gly Glu Glu Glu Thr Arg Met Trp Ala Gln Asp Gly
    50                  55                  60

Ala Leu Trp Leu Leu Pro Ala Leu Gln Glu Asp Ser Gly Thr Tyr Val
65                  70                  75                  80
```

```
Cys Thr Thr Arg Asn Ala Ser Tyr Cys Asp Lys Met Ser Ile Glu Leu
                85                  90                  95

Arg Val Phe Glu Asn Thr Asp Ala Phe Leu Pro Phe Ile Ser Tyr Pro
            100                 105                 110

Gln Ile Leu Thr Leu Ser Thr Ser Gly Val Leu Val Cys Pro Asp Leu
        115                 120                 125

Ser Glu Phe Thr Arg Asp Lys Thr Asp Val Lys Ile Gln Trp Tyr Lys
    130                 135                 140

Asp Ser Leu Leu Leu Asp Lys Asp Asn Glu Lys Phe Leu Ser Val Arg
145                 150                 155                 160

Gly Thr Thr His Leu Leu Val His Asp Val Ala Leu Glu Asp Ala Gly
                165                 170                 175

Tyr Tyr Arg Cys Val Leu Thr Phe Ala His Glu Gly Gln Gln Tyr Asn
            180                 185                 190

Ile Thr Arg Ser Ile Glu Leu Arg Ile Lys Lys Lys Glu Glu Thr
        195                 200                 205

Ile Pro Val Ile Ile Ser Pro Leu Lys Thr Ile Ser Ala Ser Leu Gly
    210                 215                 220

Ser Arg Leu Thr Ile Pro Cys Lys Val Phe Leu Gly Thr Gly Thr Pro
225                 230                 235                 240

Leu Thr Thr Met Leu Trp Trp Thr Ala Asn Asp Thr His Ile Glu Ser
                245                 250                 255

Ala Tyr Pro Gly Gly Arg Val Thr Glu Gly Pro Arg Gln Glu Tyr Ser
            260                 265                 270

Glu Asn Asn Glu Asn Tyr Ile Glu Val Pro Leu Ile Phe Asp Pro Val
        275                 280                 285

Thr Arg Glu Asp Leu His Met Asp Phe Lys Cys Val Val His Asn Thr
    290                 295                 300

Leu Ser Phe Gln Thr Leu Arg Thr Thr Val Lys Glu
305                 310                 315

<210> SEQ ID NO 6
<211> LENGTH: 18
<212> TYPE: PRT
<213> ORGANISM: Artificial Sequence
<220> FEATURE:
<223> OTHER INFORMATION: inhibits IL1RAP protein-protein interaction
<220> FEATURE:
<221> NAME/KEY: MISC_FEATURE
<222> LOCATION: (16)..(18)
<223> OTHER INFORMATION: x = any amino acid

<400> SEQUENCE: 6

Ala Gly Asp Lys Asp Arg Leu Ile Val Met Glu Asn Lys Pro Thr Xaa
1               5                   10                  15

Xaa Xaa

<210> SEQ ID NO 7
<211> LENGTH: 19
<212> TYPE: PRT
<213> ORGANISM: Artificial Sequence
<220> FEATURE:
<223> OTHER INFORMATION: inhibits IL1RAP protein-protein interaction
<220> FEATURE:
<221> NAME/KEY: MISC_FEATURE
<222> LOCATION: (16)..(19)
<223> OTHER INFORMATION: x = any amino acid

<400> SEQUENCE: 7
```

-continued

```
Ala Gly Asp Lys Asp Arg Leu Ile Val Met Glu Asn Lys Pro Thr Xaa
1               5                   10                  15

Xaa Xaa Xaa
```

PEPTIDES FOR BLOCKING IL1RAP PROTEIN-PROTEIN INTERACTION AND USES THEREOF FOR TREATMENT OF DISEASE

CROSS-REFERENCE TO RELATED APPLICATIONS

This application is a U.S. national stage entry under 35 U.S.C. § 371 of PCT International Patent Application No. PCT/US2015/062060, filed Nov. 23, 2015, which claims the benefit of U.S. Provisional Application No. 62/083,417, filed Nov. 24, 2014, the contents of each of which are incorporated herein by reference into the subject application.

BACKGROUND OF THE INVENTION

Throughout this application various publications are referred to in superscript. Full citations for these references may be found at the end of the specification before the claims. The disclosures of these publications are hereby incorporated by reference in their entireties into the subject application to more fully describe the art to which the subject application pertains.

Interleukin 1 receptor accessory protein (IL1RAP) is a member of the Toll/interleukin-1 (IL1) receptor (TIR) superfamily that has been involved in the progression or resolution of infection, asthma, allergy and anaphylaxis, cardiovascular disease, arthritis and neurodegenerative disease[1-3]. In addition, there are changes in expression of IL1RAP in CD34 positive[4], progenitor cells in Chronic Myeloid Leukemia (CML)[5], and more precisely defined stem cells in Acute Myeloid Leukemia (AML) and high-risk Myelodysplastic Syndromes (MDS)[6, 7], and also other types of cancers such as papillary thyroid carcinoma[8].

IL1RAP was originally described as a necessary partner of the interleukin 1 receptor 1 (IL1R1)[9] to initiate IL1 signaling. However, IL1RAP participates in other signaling pathways through interaction with several receptors other than IL1R1 such as the interleukin-1 receptor 2 (IL1R2)[10], the interleukin 33 receptor (ST2)[11-13], and the receptor for interleukin 36 family (IL1RL2)[14]. More recently, the receptor tyrosine kinase (RTK) KIT was also shown to interact with IL1RAP in mast cells to initiate their degranulation[15]. In murine cells, IL1RAP forms a complex with the glycoprotein SIRPα1 to activate Akt and Erk in response to IL1β stimulation[16]. As IL1RAP can participate in different signaling pathways, its direct targeting should disrupt more than one physiological process relevant for a broad spectrum of diseases.

Blockade of IL1RAP interactions is also appealing due to the relatively low or absent expression on most types of healthy HSPC and mature cell populations (except monocytes and some lymphocyte populations), and the absence of major phenotype in IL1RAP null mice. Targeting of IL1RAP was proposed for the treatment of inflammatory diseases[17]. Additionally, several drugs have been developed for the targeting of IL1 signaling in diseases other than leukemia. These drugs act to neutralize IL1 by interfering with the production of IL1β or posttranslational processing of IL1[18] and a few are currently being investigated for leukemia (ClinicalTrials.gov NCT01260545)[2]. A cytotoxic antibody against IL1RAP has been developed and tested in CML cells and more recently in AML primary cells[4, 7]. The Fc portion of this antibody mediates antibody-dependent cellular cytotoxicity (ADCC), likely by natural killer (NK) cells which induce cell death of IL1RAP expressing cells. Here maximal antibody response activity depends on the availability of NK cell populations in leukemia and the assumption that ADCC is the dominant mechanism of action in leukemia patients. Then the focus of current targeting strategies has not been directly placed in IL1RAP but in the IL1 cytokine itself, the IL1R natural antagonist IL1Ra or the IL1β/IL1R1 interaction.

IL1RAP is not just a surface label that can be used to direct ADCC to leukemia cells, but IL1RAP function is indeed critical for AML stem cells. Inhibition of IL1RAP by lentiviral shRNAs diminished the ability of AML cells (or high-risk MDS patient mononuclear cells) to form colonies in methylcellulose, increased cell death of AML cells in vitro[6] and led to a significant reduction of leukemic infiltration of the hematopoietic organs in a xenotransplantation model (Barreyro unpublished results), indicating that IL1RAP functions to promote cell survival and growth in leukemia. So far, no inhibitors of the function of IL1RAP have been developed.

The present invention addresses inhibitors of IL1RAP protein-protein interactions that can be used in treatment of a broad spectrum of diseases and conditions.

SUMMARY OF THE INVENTION

The invention provides methods of treating a disease or condition in a subject in which it is desirable to inhibit interleukin 1 receptor accessory protein (IL1RAP) protein-protein interaction, where the methods comprise administering to the subject an agent comprising a peptide in an amount effective to inhibit IL1RAP protein-protein interaction.

The invention also provides agents for treating a disease or condition in a subject in which it is desirable to inhibit interleukin 1 receptor accessory protein (IL1RAP) protein-protein interaction, where the agents comprise a peptide that inhibits IL1RAP protein-protein interaction.

The invention further provides a synthetic peptide consisting of amino acid sequence AGDKDRLIVMENKPTRPV (SEQ ID NO:1) or amino acid sequence AGDKDRLIVMENKPTHGID (SEQ ID NO:2).

The invention still further provides methods of screening for a candidate agent for treating cancer, chronic myeloid leukemia (CML), acute myeloid leukemia (AML), myelodysplastic syndrome (MDS), papillary thyroid carcinoma, infection, asthma, allergy, anaphylaxis, cardiovascular disease, arthritis, neurodegenerative disease, and/or inflammatory disease, the method comprising testing whether the agent inhibits interleukin 1 receptor accessory protein (IL1RAP) protein-protein interaction, wherein an agent that inhibits IL1RAP protein-protein interaction is a candidate agent for treating cancer, chronic myeloid leukemia (CML), acute myeloid leukemia (AML), myelodysplastic syndrome (MDS), papillary thyroid carcinoma, infection, asthma, allergy, anaphylaxis, cardiovascular disease, arthritis, neurodegenerative disease, and/or inflammatory disease.

BRIEF DESCRIPTION OF THE DRAWINGS

FIG. 2. Sequence alignment of IL1R1 and IL1R2. Amino acid sequence alignment of human IL1R1 (SEQ ID NO:4) with human IL1R2 (SEQ ID NO:5) using ClustalW[27, 28]. Strictly conserved residues, conserved substitutions (according to the ClustalW defined strong groups: STA, NEQK, NHQK, NDEQ, QHRK, MILV, MILF, HY or FYW) and partially conserved substitutions are highlighted (according to the clustalw defined weak groups: CSA, ATV, SAG, STNK, STPA, SGND, SNDEQK, NDEQHK, NEQHRK, FVLIM or HFY). The filled circles above and below the aligned sequences indicate, respectively, the residues involved in IL1R1-IL1RAP and IL1R2-IL1RAP interactions within 4.5 angstroms.

FIG. 3A-3C. IL1RAP peptides of interference reduce cell growth. A) Image of the crystal structure of the extracellular domains of the IL1RAP (sphere representation) bound to IL1R1 (ribbon representation) (PDB ID:4DEP) is depicted with peptide of interference P1 (sphere representation). B) Scheme of the IL1RAP peptides of interference with the respective amino acid positions indicated with numbers. Peptide 1 (p1) (SEQ ID NO:1), Peptide 2 (p2) (SEQ ID NO:2) C) THP-1 cells were exposed to scrambled peptide (scrambled), or IL1RAP peptides (P1 and P2) at the indicated concentrations or left untreated (dashed line) and evaluated for cell viability determined by trypan blue staining and manual counts at 12 and 24 hours. Error bars represent the standard error of the mean of two independent experiments.

DETAILED DESCRIPTION OF THE INVENTION

Figure 1A:
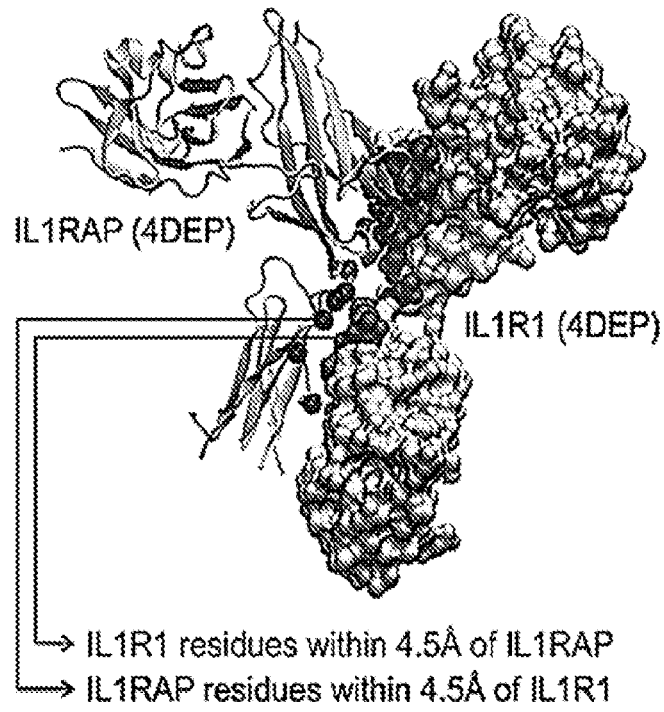
FIG. 1A-1B. In silico design of IL1RAP peptides of interference. A) Crystal structure of the extracellular domains of the IL1R1 (sphere representation) bound to IL1RAP (ribbon representation) (PDB ID: 4DEP) is depicted with the aminoacids at the receptor-coreceptor contact interphase (sphere representation) B) structural superimposition of 4DEP and 3O4O.

The invention provides a method of treating a disease or condition in a subject in which it is desirable to inhibit interleukin 1 receptor accessory protein (IL1RAP) protein-protein interaction, the method comprising administering to the subject an agent comprising a peptide in an amount effective to inhibit IL1RAP protein-protein interaction.

The invention also provides an agent for treating a disease or condition in a subject in which it is desirable to inhibit interleukin 1 receptor accessory protein (IL1RAP) protein-protein interaction, the agent comprising a peptide that inhibits IL1RAP protein-protein interaction.

The disease or condition can be, for example, one or more of cancer, chronic myeloid leukemia (CML), acute myeloid leukemia (AML), myelodysplastic syndrome (MDS), papillary thyroid carcinoma, infection, asthma, allergy, anaphylaxis, cardiovascular disease, arthritis, neurodegenerative disease, and inflammatory disease.

The peptide can target, for example, conserved residues of a common interface of IL1RAP that interacts with interleukin 1 receptor 1 (IL1R1), interleukin 1 receptor 2 (IL1R2), interleukin 1 receptor-like 1 (IL1RL1), interleukin 1 receptor-like 2 (IL1RL2), signal-regulatory protein alpha (SIRPA), ST2, KIT, Fms-like tyrosine kinase 3 (FLT3) (including its mutant variants, e.g. FLT3-internal tandem duplication, or FLT3 juxtamembrane mutants), macrophage colony-stimulating factor receptor (MCSFR), toll-like receptor (TLR), or other proteins interacting through this molecular interface.

The peptide can, for example, comprise 18-30 amino acids that include one of the following amino acid sequences: AGDKDRLIVMENKPTRPV (SEQ ID NO:1), AGDKDRLIVMENKPTHGID (SEQ ID NO:2), AGDKDRLIVMENKPTXXX (SEQ ID NO:6) or AGDKDRLIVMENKPTXXXX (SEQ ID NO:7). The peptide can, for example, consists of amino acid sequence AGDKDRLIVMENKPTRPV (SEQ ID NO:1) or AGDKDRLIVMENKPTHGID (SEQ ID NO:2).

The invention further provides a synthetic peptide consisting of amino acid sequence AGDKDRLIVMENKPTRPV (SEQ ID NO:1) or amino acid sequence AGDKDRLIVMENKPTHGID (SEQ ID NO:2).

The peptides can be conjugated to different agents, for example, a cytotoxic agent, a polyethylene glycol (PEG) or a nanoparticle. The cytotoxic agent can be, for example, a small molecule of 2,000 daltons or less, or 1,000 daltons or less, or 500 daltons or less. The PEG can have a molecular weight, for example, of 200-2,000 daltons or more. Preferably the nanoparticle is between 1 and 100 nanometers in size.

The invention still further provides a method of screening for a candidate agent for treating cancer, chronic myeloid leukemia (CML), acute myeloid leukemia (AML), myelodysplastic syndrome (MDS), papillary thyroid carcinoma, infection, asthma, allergy, anaphylaxis, cardiovascular disease, arthritis, neurodegenerative disease, and/or inflammatory disease, the method comprising testing whether the agent inhibits interleukin 1 receptor accessory protein (IL1RAP) protein-protein interaction, wherein an agent that inhibits IL1RAP protein-protein interaction is a candidate agent for treating cancer, chronic myeloid leukemia (CML), acute myeloid leukemia (AML), myelodysplastic syndrome (MDS), papillary thyroid carcinoma, infection, asthma, allergy, anaphylaxis, cardiovascular disease, arthritis, neurodegenerative disease, and/or inflammatory disease.

The agents or peptides can be administered to subjects using routes of administration known in the art. The administration can be systemic or localized to a specific site. Routes of administration include, but are not limited to, intravenous, intramuscular, intrathecal or subcutaneous injection, oral or rectal administration, and injection into a specific site.

The invention further provides a pharmaceutical composition comprising any of the agents or peptides identified herein and a pharmaceutically acceptable carrier. As used herein, a "pharmaceutically acceptable carrier" is (i) compatible with the other ingredients of the composition without rendering the composition unsuitable for its intended purpose, and (ii) suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers include any of the standard pharmaceutical carriers such as phosphate buffered saline solutions, water, and emulsions such as oil/water emulsions and microemulsions.

This invention will be better understood from the Experimental Details that follow. However, one skilled in the art will readily appreciate that the specific methods and results discussed are merely illustrative of the invention as described more fully in the claims that follow thereafter.

EXPERIMENTAL DETAILS

Introduction and Overview

Specific peptides were designed to interfere with the oligomerization of interleukin 1 receptor accessory protein (IL1RAP) with its receptors partners (including KIT, and FLT3, known key drivers of AML pathogenesis, which the inventors recently identified to interact with IL1RAP in AML cells (unpublished). These peptides enable specific interruption of IL1RAP mediated signaling representing a fundamentally novel therapeutic approach. As an example, interfering peptides were shown to lead to inhibition of downstream signaling and significant growth inhibition of IL1RAP-dependent leukemia cells.

Materials and Methods

Peptide Design.

To interrupt the interaction between the extracellular domains of IL1RAP and its associated molecules small peptides were designed utilizing the crystal structures of the extracellular complexes of IL1RAP, IL1R1 and IL1β (PDB ID: 4DEP[19]) and IL1RAP, IL1R2 and IL1β (PDB ID: 3O4O[20]) available in the Protein Data Bank (PDB)[21]. Contacts between amino acids from two different polypeptide chains (IL1RAP against IL1R1 and IL1R2) were defined as having any two atoms at a maximum distance of 4.5 Angstroms, which sufficiently encompasses Van der Waals, hydrogen bond, and most hydrophobic interactions. Structural superimposition between the two complexes was carried out using the program STAMP (STructural Alignment of Multiple Proteins)[22] as made available in the program VMD (Visual Molecular Dynamics)[23].

Cell Lines.

The AML cell line THP-1 was grown in RPMI medium supplemented with 10% Fetal Bovine Serum (FBS), 10 mM HEPES, 1 mM Sodium pyruvate, 0.05 mM betamercaptoethanol and 1% penicillin/streptomycin.

Peptide Resuspension and Cell Line Treatment.

Two specific peptides (P1: AGDKDRLIVMENKPTRPV (SEQ ID NO:1) and P2: AGDKDRLIVMENKPTHGID (SEQ ID NO:2)) and one scrambled control peptide (LKDMPGRPNERDKVAlTV (SEQ ID NO:3)) were synthesized by Genscript (Piscataway, N.J.) using stepwise SPPS chemical methods and purified by HLPC (purity >98%). Peptides were free of trifluoroacetate. Lyophilized peptides were aliquoted and resuspended in 0.15M PBS pH 7.0 before use. THP-1 cells were seeded at $0.5 \times 10^6$ cells/ml and treated with control, vehicle or specific peptides at the indicated concentrations every 4 hours during the indicated periods of time.

Cell Viability and Clonogenic Assays.

Cell viability was assessed at the indicated time points by trypan blue staining and manual cell counts. Viable cells were plated in methylcellulose (StemCell technologies H4434, or R&D HSC002SF) at 1000 cells/ml in 6-well plates for cell lines and at $5 \times 10^4$ cells/ml for bone marrow mononuclear cells (BMMNC). Cells were incubated at 37° C. and 5% $CO_2$. Colonies were scored after 7 days or 14 days in culture for cell lines or primary cells, respectively.

AML Clonogenic Assays.

Primary AML mononuclear cells derived from peripheral blood were seeded in cellgro media with cytokines (FLT3L 300 ng/ml, TPO 100 ng/ml, SCF 300 ng/ml and IL3 60 ng/ml) and antibiotic. Cells were treated with IL1RAP peptides of interference or scrambled control at 300 uM for 4 hours. After that period, cell viability was assessed by trypan blue staining and manual cell counts. Viable cells were plated in methylcellulose (StemCell technologies H4434, or R&D HSC002SF) at $5 \times 10^4$ cells/ml in 6-well plates. Cells were incubated at 37° C. and 5% $CO_2$. Colonies were scored after 14 days in culture.

Flow Cytometric Determination of Cell Death.

In order to determine viability after peptide treatment, $1 \times 10^4$ THP-1 cells were washed with PBS and mixed with pre-diluted PE-conjugated Annexin V (BD Pharmigen) and DAPI. Cells were stained at room temperature for 15 minutes and suspended in 0.2 ml of Annexin V-FLUOS incubation buffer (Roche) for analysis.

Cell Cycle Analysis.

Cell cycle analysis was performed by staining with propidium iodide (PI). In brief, $1 \times 10^6$ THP-1 cells after treatment with peptides were rinsed with PBS, fixed Fixation Buffer (BD Cytofix™ fixation buffer) for 30 min at 4° C. 5 ml of cold 70 to 80% ethanol were added to the cells while vortexing and the suspension was stored overnight at −20° C. Cells were washed twice (first with PBS and then with 1×PBS, 2% FBS) and spun down for 10 minutes at 1,500 rpm. Cell pellet was resuspended in 0.5 mL of PI/RNase Staining Buffer (BD Pharmingen® PI/RNase staining buffer) and incubated 15 minutes at room temperature and immediately analyzed by flow cytometry using a FACSAria II Special Order System (BD Biosciences, San Jose, Calif.).

Cell Morphology.

$1 \times 10^4$ THP-1 cells after treatment with peptides were rinsed with PBS and 0.1 ml of cell suspension was cytospun onto polylysine coated slides at minimum speed for 4 minutes in a cytocentrifuge (StatSpin Cytofuge). Slides were stained according to manufacturer's protocol using the Romanowsky staining Diff-Quick (IMEB) kit. Cells were imaged with an Axiovert 200M microscope (Zeiss) and Olympus SZ61 microscope.

Preparation of Cell Lysates and Immunoblotting.

$3 \times 10^5$ THP-1 cells after treatment with peptides, were lysed with modified RIPA buffer (Tris-HCl 50 mM pH7.4, NP-40 1%, Na-deoxycholate 0.25%, NaCl 150 mM, EDTA 1 mM, PMSF 1 mM, Roche protease inhibitor cocktail Mini complete 1×, $Na_3VO_4$ 1 mM, NaF 1 mM and β-glycerophosphate 20 mM). The lysate was incubated in orbital shaker 4° C. 15-30 min. in a cold room. Then, cells were spun at 14,000×g 4° C. for 15 min and the supernatant was transferred to a pre-cooled tube. Protein concentration in cell lysate was determined, 25 µg of lysate were mixed with 2×SDS loading buffer, boiled for 5 min, and loaded in 8% SDS-polyacrylamide gel. Proteins were transferred to a PVDF membrane and analyzed by western blot with indicated antibodies. Membranes were stripped as needed using a previously published protocol[24]. For immunoblotting, the following antibodies were used: phospho-FLT3 (Tyr591) Mouse monoclonal antibody (Cell signaling #3466), anti-phospho IRAK (T209-abcam 61799), phospho-STAT3 Tyr705) antibody (Cell signaling #9131) and Actin Antibody (C-11 sc-1615). Membranes were developed using Pierce ECL Western Blotting Substrate (thermo) or SuperSignal West Femto Chemiluminescent Substrate (thermo).

Results and Discussion

Design of IL1RAP Inhibitory Peptides.

The development of small molecules that can specifically disrupt IL1RAP-receptor interactions will be a valuable tool not only to target IL1RAP-mediated signaling in AML, MDS, and other diseases, but it will also facilitate study of IL1RAP protein-protein interactions. Therefore, studies were designed to interrupt the interaction between the interacting domains of IL1RAP and its associated molecules with small peptides of interference.

Crystallographic data were used to design a peptide to occupy the interaction surface in the extracellular domain of the IL1RAP-IL1R1 as well as the IL1RAP-IL1R2 complexes (FIG. 1A). Available in the Protein Data Bank (PDB)[21] are the structures of the interacting extracellular domains of IL1RAP in complex with IL1R1 (PDB ID: 4DEP[19]) and with IL1R2 (PDB ID: 3O4O[20]). The complex in 4DEP contains 3 polypeptide chains: 1) IL1β as chain A, covering residues 1-151, 2) IL1RAP as chain B, covering residues 7-310 and 3) IL1R1 as chain C, covering residues 3-326. Similarly, the complex in 3O4O contains 3 polypeptide chains: 1) IL1β as chain A, covering residues 1-152, 2) IL1R2 as chain B, covering residues 4-326 and 3) IL1RAP as chain C, covering residues 5-310. The crystal structure of the complex in 4DEP or 3O4O reveals that the largest interface is formed between IL1R1 and IL1β (similarly for IL1R2), with an average of 41 residues involved. Such a large interface is produced by the wrapping of IL1β by the two flexibly linked immunoglobulin domains of IL1R1. IL1RAP also physically interacts with the IL1β polypeptide, averaging 15 residues at the contact area. The contact interface between IL1RAP and either IL1R1 or IL1R2 is formed by 16 residues on average.

Figure 1B:
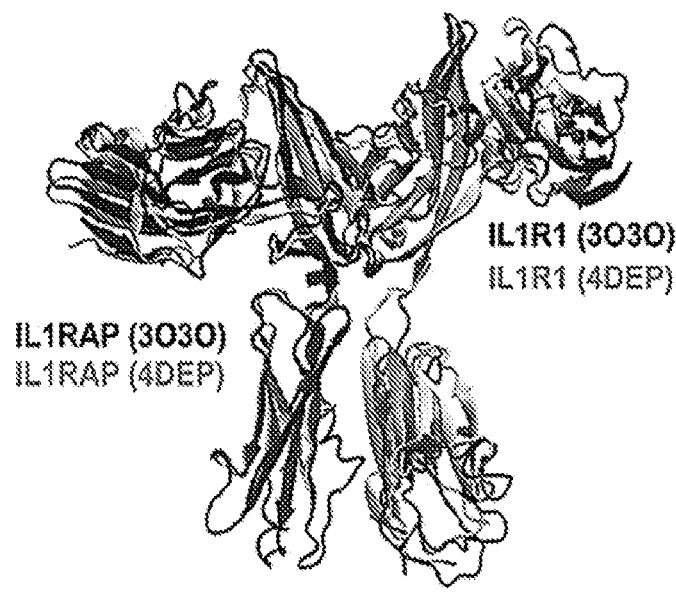

The above mentioned complexes are superimposable (see methods) (FIG. 1B). The structural overlay reveals that IL1RAP utilizes the same interface to interact with both receptors IL1R1 and IL1R2. Closer scrutiny of the receptor-coreceptor interface exposes the particular residues of IL1RAP and IL1R1/IL1R2 that are in contact (FIG. 1A). These contacting residues between IL1RAP and its receptors are also highlighted on the sequence alignment in FIG. 2. Most of the residues from IL1R1 and IL1R2 in contact with IL1RAP are conserved or at least semi-conserved (with a few exceptions). Out of 12 aligned residues within 4.5 angstroms, 4 are identical, 5 conserved (meaning that general properties of the residue side-chains are conserved), 1 semi-conserved (D120-S134 who only share the characteristic of being polar) and 2 unrelated substitutions.

The design of peptides of interference was based on the idea that they should resemble the residue identities in the interaction surface of IL1RAP and its receptors. Therefore, residues found at the interaction surface of IL1R1 or IL1R2 with IL1RAP were considered in the design of the peptides. A linear path was found in the structures that traverses most of the common interface residues; peptides were designed that combine most of these common contacts (FIG. 3A). This strategy is potentially powerful because the designed peptides would simultaneously interrupt both interactions, and including interactions with other molecules.

IL1RAP Peptides of Interference Suppress Growth of AML Cells.

Figure 4:
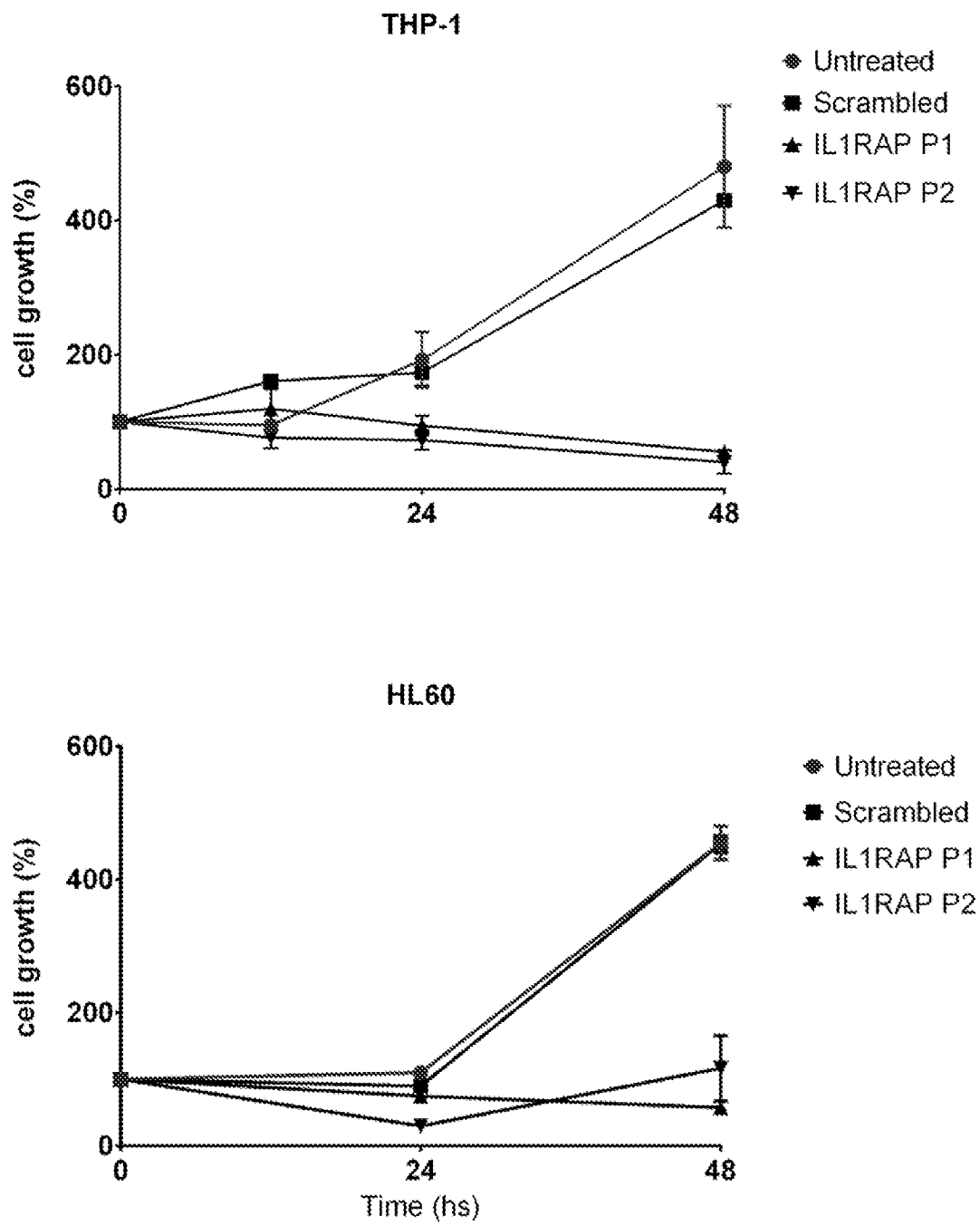
FIG. 4. IL1RAP peptides of interference reduce cell growth in two different leukemia cell lines. THP-1 cells (a human monocytic cell line derived from an acute monocytic leukemia patient) (upper panel) and HL60 cells (human promyelocytic leukemia cells) (lower panel) were exposed to scrambled peptide (scrambled), or IL1RAP peptides (P1 and P2) at 300 µM concentrations or left untreated and evaluated for cell viability determined by trypan blue staining and manual counts at the indicated durations of exposure. Error bars represent the standard error of the mean of two independent experiments.
Figure 5A:
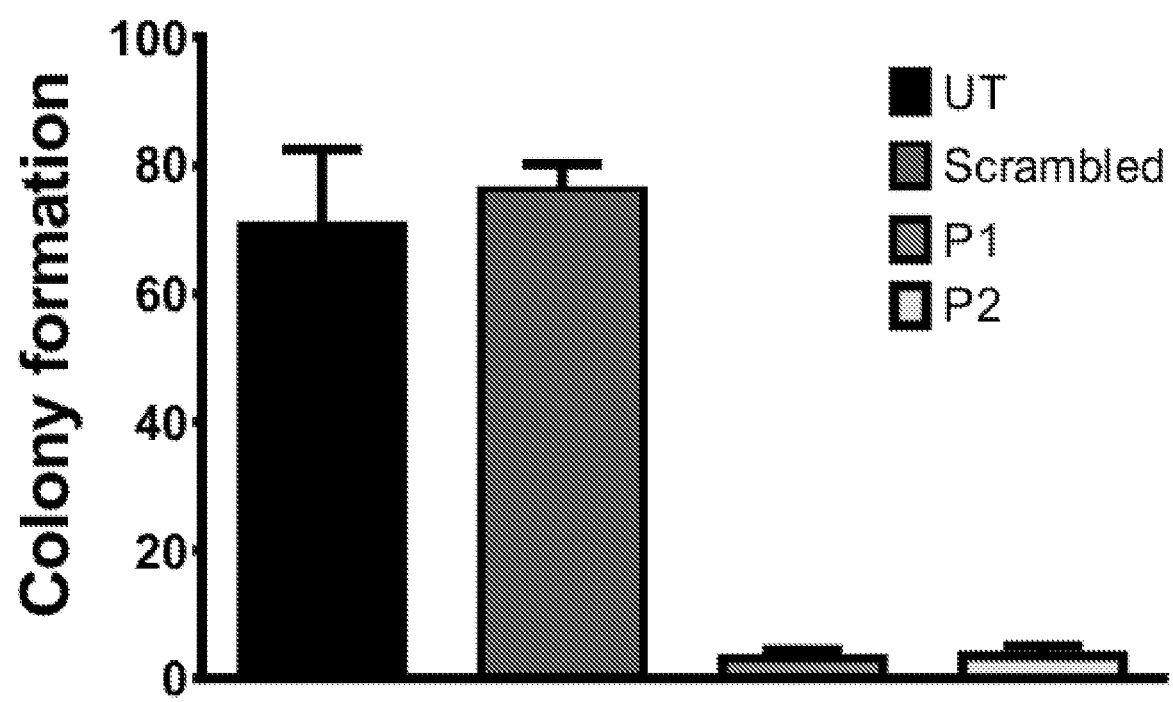
FIG. 5A-5B. A) IL1RAP blockade causes reduced clonogenic potential of AML cells. THP-1 cells were exposed to 300 µM IL1RAP peptides (P1 and P2), scrambled control peptide (scrambled) or left untreated (UT) and evaluated for colony formation capacity in methylcellulose. The results are expressed as total number of colonies/1000 plated cells. Error bars represent the standard deviation of two replicates. Furthermore, primary human AML cells from patients were treated with peptides and evaluated in the same way (FIG. 5B). B) IL1RAP blockade causes reduced clonogenic potential of primary AML mononuclear cells. AML mononuclear cells derived from peripheral blood were exposed to 300 µM IL1RAP peptides (P1 and P2), scrambled control peptide (scrambled) or left untreated (UT) for 4 hours and evaluated for colony formation capacity in methylcellulose. The results are expressed as total number of colonies/50,000 plated cells. Error bars represent the standard deviation of two replicates.
Figure 5B:
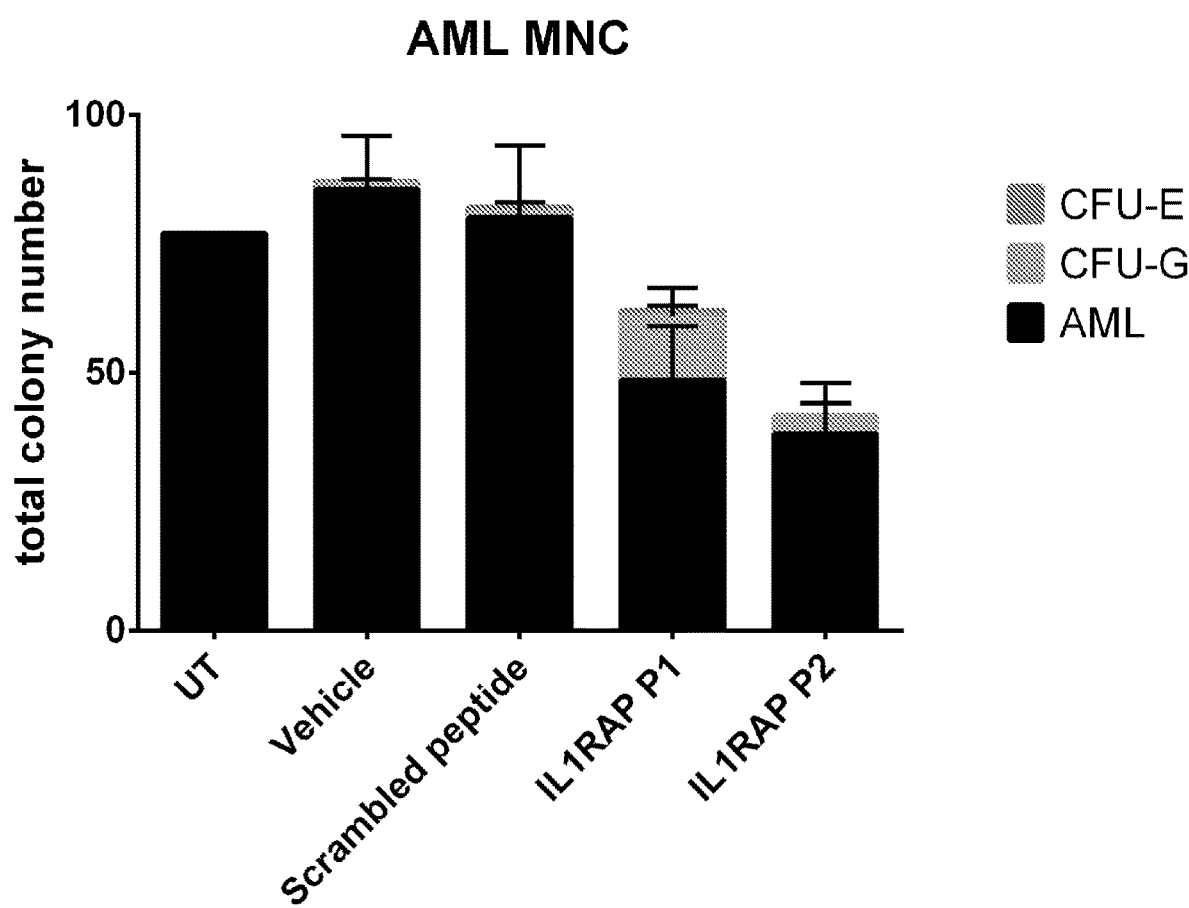

Since knockdown of IL1RAP with lentivirally expressed shRNAs in THP-1 cells reduced cell survival[6], it was determined whether specific or scrambled control peptides affected cell viability in the IL1RAP-positive cell line THP-1. THP-1 cells were treated with either different peptides of interference (P1 and P2 in FIG. 3B) or scrambled control peptide, or the cells were left untreated. Peptides were added at 4 hour intervals, for a period of 12 hours. Specific peptides P1 and P2, but not control peptide, caused loss of viability and growth suppression of THP1 cells (FIG. 3C, 4). In addition, IL1RAP peptides of interference P1 and P2 led to inhibition of leukemic colony formation of THP-1 cells in comparison to the scrambled control peptide (FIG. 5).

IL1RAP Peptides of Interference do not Suppress Growth of Healthy Bone Marrow Mononuclear Cells.

Figure 6:
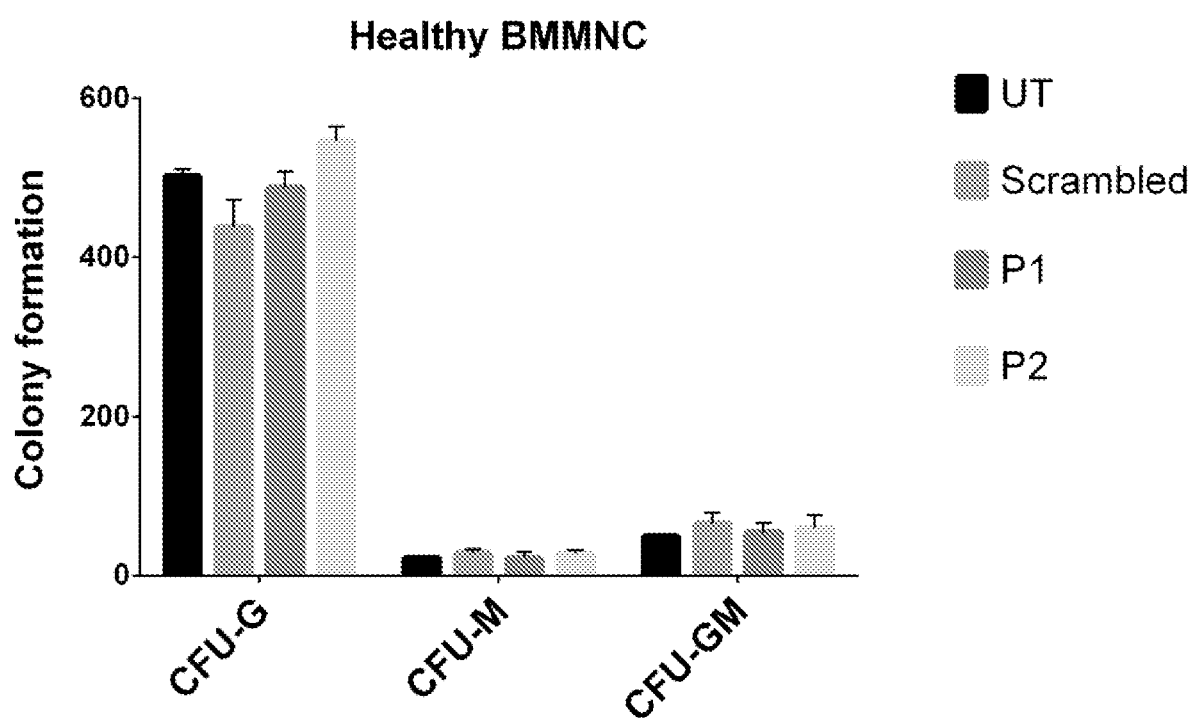
FIG. 6. IL1RAP peptides of interference do not reduce clonogenic potential of healthy bone marrow mononuclear cells (BMMNC). BMMNC were exposed to scrambled peptide (scrambled), or IL1RAP peptides (P1 and P2) for 4 hours at 300 µM concentrations or left untreated (UT) and evaluated for colony formation capacity in methylcellulose. Colonies were scored at 14 days. The results are expressed as total number of colonies/5×10$^4$ plated cells. Error bars represent the standard deviation of two replicates.

In contrast to the effects of peptides P1 and P2 on AML cells, no inhibitory effects of these peptides were observed on healthy control bone marrow mononuclear cells (FIG. 6). These include healthy stem and progenitor cells that do not express IL1RAP.[6]

IL1RAP Peptides of Interference Induced Apoptosis and/or Cell Cycle Arrest in AML Cells.

Figure 7:
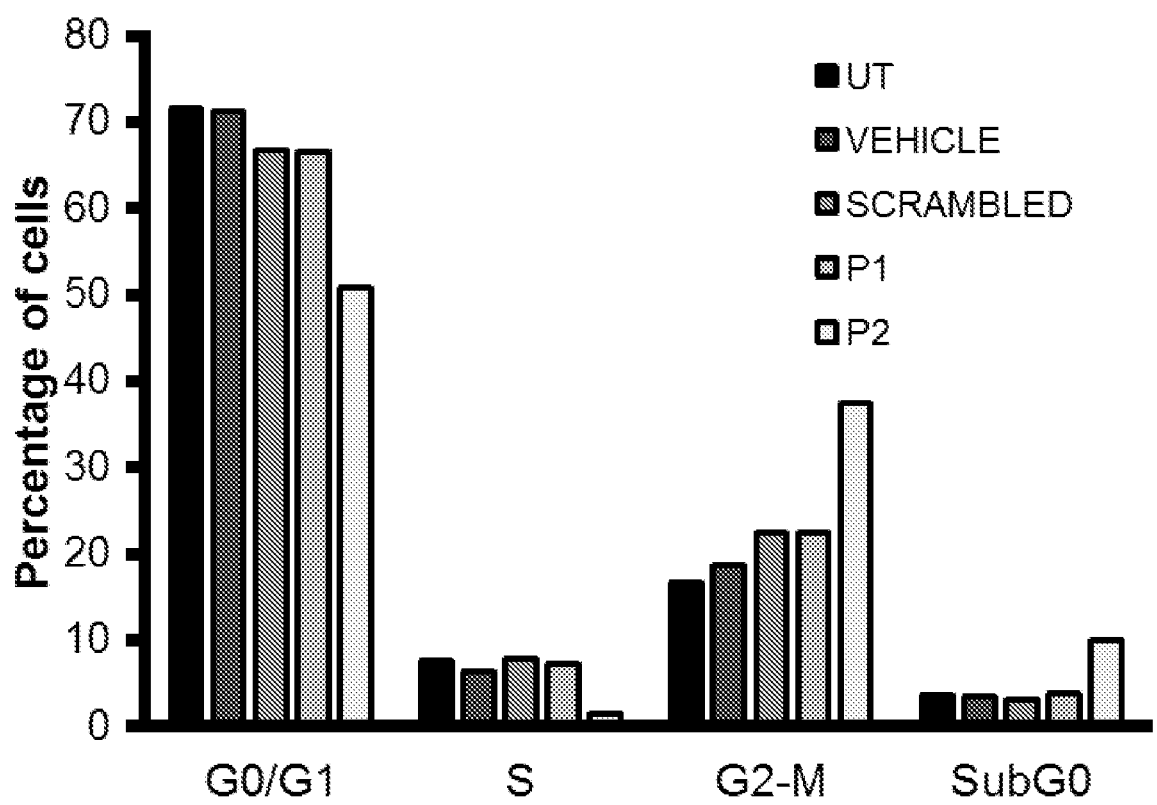
FIG. 7. IL1RAP blockade causes apoptosis and cell cycle arrest in G2 of IL1RAP dependent human leukemia cells. THP1 cells were exposed to 300 µM IL1RAP peptides (P1 and P2), scrambled control peptide (scrambled), peptide buffer (vehicle) or left untreated (UT) and evaluated for cell cycle progression determined by flow cytometry.
Figure 8:
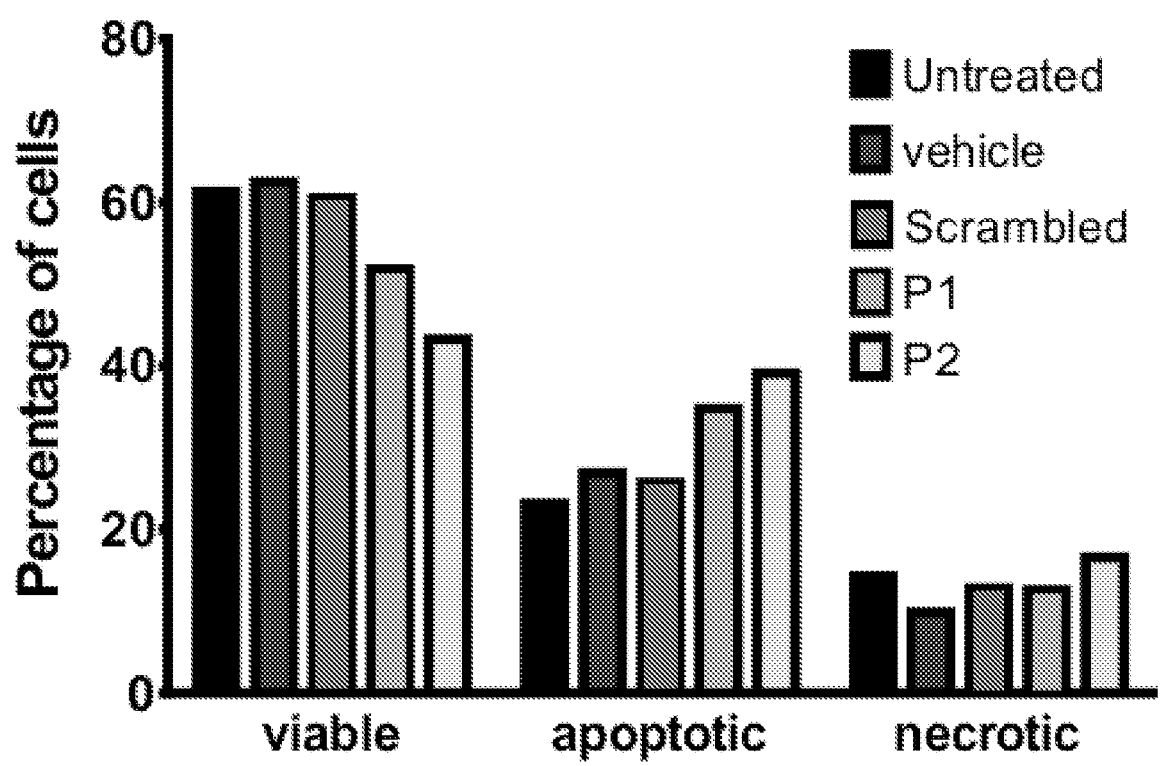
FIG. 8. IL1RAP blockade causes cell death of IL1RAP dependent human leukemia cells. THP1 cells were exposed to 300 µM IL1RAP peptides (P1 and P2), scrambled control peptide (scrambled), peptide buffer (vehicle) or left untreated (UT) and evaluated for cell viability determined by Annexin V/DAPI staining and flow cytometry. The results are expressed as percentage of total cells.

The phenotypic effects of the IL1RAP interaction blockade in AML cells were assessed in vitro in THP-1 cells. THP-1 cells treated with 300 µM of either IL1RAP peptides P1 or P2 or control peptide were stained with Annexin V and DAPI and subjected to flow cytometric analysis. Changes in cell cycle were also analyzed by Propidium iodide staining and flow cytometry. THP-1 cells underwent a moderate cell cycle arrest in G2 (FIG. 7) in the presence of IL1RAP peptide P2 but not control peptide (scrambled) or peptide buffer (vehicle). At 24 hours after initial treatment, IL1RAP specific peptides P1 and P2 caused an increase of apoptosis as determined by Annexin V/DAPI staining (FIG. 8). THP-1 cells treated with IL1RAP blocking peptides demonstrated a higher degree of cell death (DAPI$^+$/Annexin V$^+$); 39% (P2) and 35% (P1) of cells were considered apoptotic upon IL1RAP blockade. IL1RAP peptides P1 and P2 showed an overall reduction in viability (DAPI$^+$/Annexin V$^+$) of 28% (P2) and 14% (P1) in comparison to the scrambled control peptide. In addition PI staining showed an increase of subG0 for IL1RAP peptide P2 that indicates increased levels of apoptosis (FIG. 7).

IL1RAP Peptides of Interference Induced Changes in Morphology Indicative of Differentiation of AML Cells.

Figure 9:
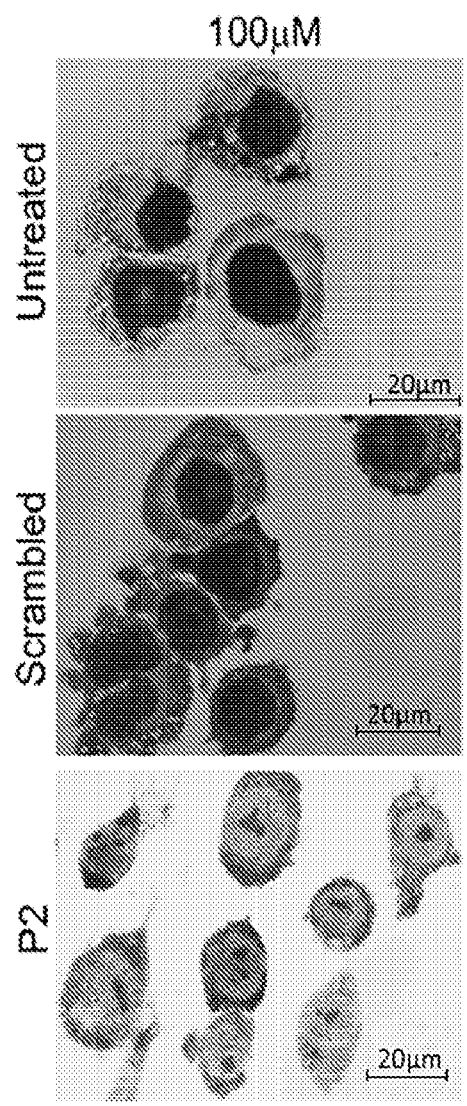
FIG. 9. IL1RAP blockade changes in cell morphology of IL1RAP dependent human leukemia cells. THP1 cells were exposed to 100 µM IL1RAP peptide P2, scrambled control peptide (scrambled), peptide buffer (vehicle) or left untreated and evaluated for cell morphology.

THP-1 monocyte cells can differentiate into macrophage-like cells. During the process of differentiation cells become adherent and adjust their morphology. The THP-1 cells that remained viable after 24 hours of treatment with P1 and P2 showed substantial changes in morphology which could be indicative of monocytic differentiation (FIG. 9). In contrast, cells treated with scrambled peptide maintained a blast-like morphology (FIG. 9).

IL1RAP Peptides of Interference Affect IL1 and FLT3 Signaling in AML Cells.

Figure 10:
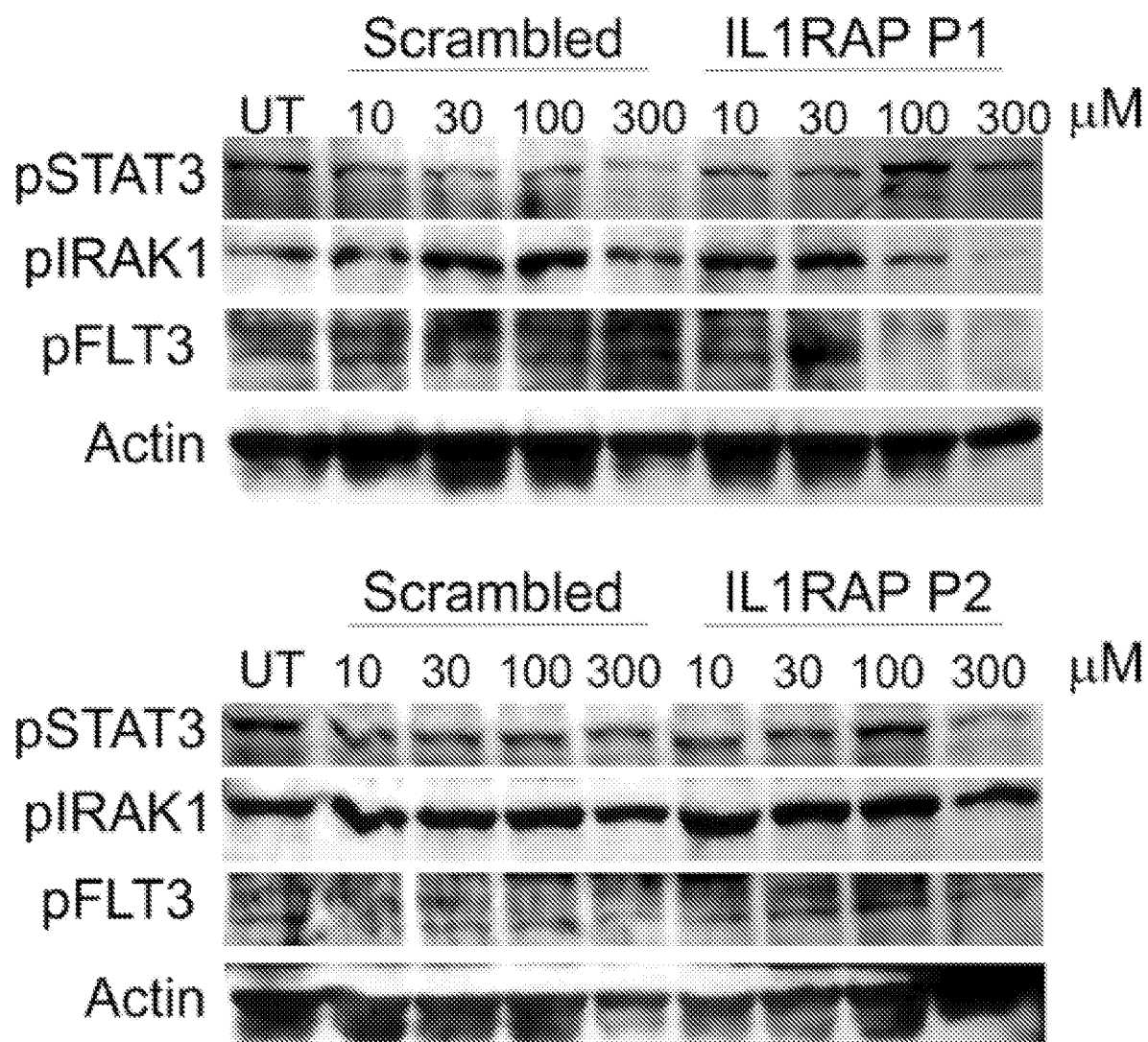
FIG. 10. IL1RAP peptides of interference. THP1 cells were exposed to increasing concentrations of IL1RAP peptides P1 (upper panel) and P2 (lower panel), scrambled control peptide (scrambled) or left untreated (UT) and evaluated for changes in phospho-IRAK1, phospho-FLT3 and phospho-STAT3 by western blot.
Figure 11:
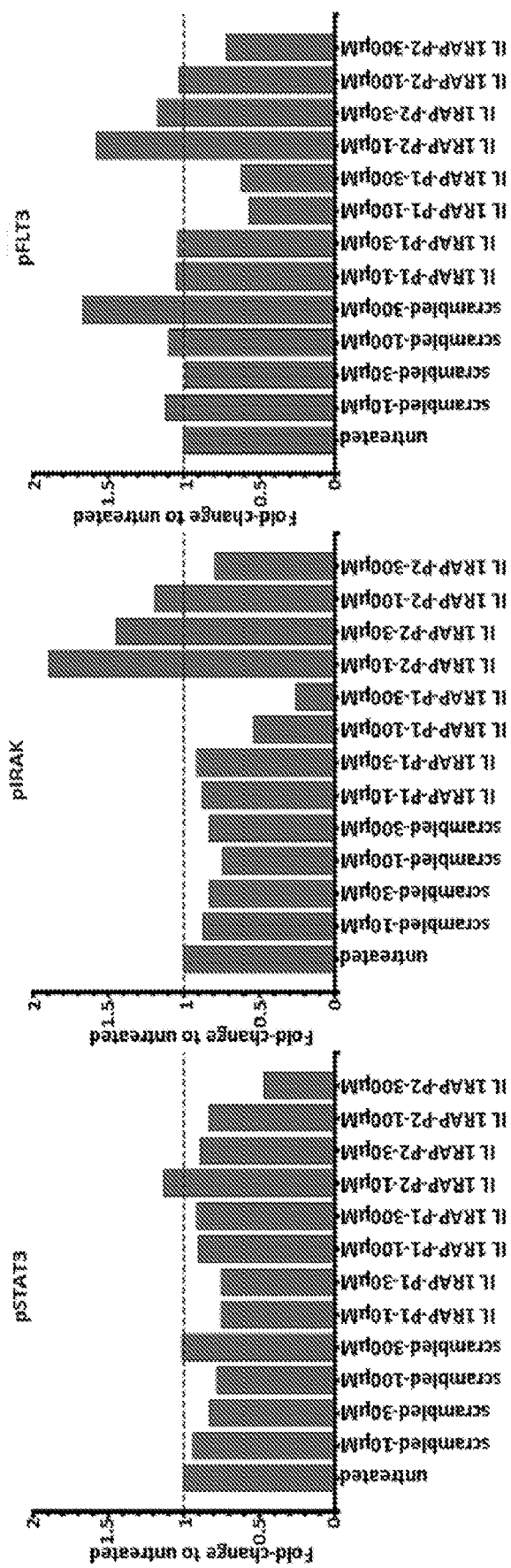
FIG. 11. Bar graphs show an Image J quantification of western blots from FIG. 10. Dotted line indicates the level of untreated sample. Values are expressed as fold-change to untreated sample.

In active IL1 signaling, the interaction of IL1RAP with IL1R1 leads to the recruitment and phosphorylation of the interleukin 1 receptor associated kinase 1 (IRAK1). To assess whether IL1RAP peptides of interference were effective in blocking IL1 signaling, the phosphorylation levels of IRAK1 were determined 48 hours after treatment with IL1RAP specific peptides or scrambled control. A profound concentration dependent reduction of phospho-IRAK1 was observed in THP-1 cells treated with IL1RAP peptide P1 in comparison with scrambled control peptide (FIGS. 10, 11). In addition, both IL1RAP specific peptides P1 and P2 showed reduced phosphorylation levels in phospho-FLT3, a receptor tyrosine kinase that also interacts with IL1RAP in leukemia cells (Barreyro unpublished results). It is possible that IL1RAP peptides of interference P1 and P2 have different binding affinity because similar changes were not observed in phosphorylation of IRAK1 at 48 hs. In addition, levels of phospho-STAT3, a transcription factor that is activated by IL1 and FLT3 signaling[25,26], changed at 48 hs after the initial treatment with IL1RAP peptide P2 to a greater extent than with IL1RAP peptide P1 (FIGS. 10, 11). This finding suggests that IL1RAP peptides of interference successfully block IL1 and FLT3 signaling and attenuate downstream activation of signal transducer and activator of transcription STAT3 through the interleukin (IL)-1 and FLT3 signaling pathways by blocking IL1R1/IL1RAP and IL1RAP/FLT3 receptor interactions in leukemic cells.

The present invention provides a functional interference strategy to inhibit IL1RAP function, independent of current antibody-based strategies which use IL1RAP solely as a surface label to trigger/activate an immune response against IL1RAP-expressing cells, independent of whether IL1RAP plays an actual functional role for these cells.

In contrast to the present invention of using peptides of interference to block IL1RAP protein-protein interaction, antibody-based approaches are thought to mediate anti-tumor efficacy via antibody-dependent cellular cytotoxicity (ADCC) via NK cell-mediated induction of cell death. Unlike the present approach, antibody-based approaches are likely to have limited therapeutic efficacy in patients with diseases such as AML and MDS who are immunocompromised and will have impaired ADCC.

REFERENCES

1. Allan, S. M., Tyrrell, P. J. & Rothwell, N. J. Interleukin-1 and neuronal injury. *Nat Rev Immunol* 5, 629-640 (2005).
2. Dinarello, C. A., Simon, A. & van der Meer, J. W. Treating inflammation by blocking interleukin-1 in a broad spectrum of diseases. *Nature reviews. Drug discovery* 11, 633-652 (2012).
3. Liew, F. Y., Pitman, N. I. & McInnes, I. B. Disease-associated functions of IL-33: the new kid in the IL-1 family. *Nat Rev Immunol* 10, 103-110 (2010).
4. Järås, M. et al. Isolation and killing of candidate chronic myeloid leukemia stem cells by antibody targeting of IL-1 receptor accessory protein. *Proc Natl Acad Sci USA* 107, 16280-16285 (2010).
5. Gerber, J. M. et al. Genome-wide comparison of the transcriptomes of highly enriched normal and chronic myeloid leukemia stem and progenitor cell populations. *Oncotarget* 4, 715-728 (2013).
6. Barreyro, L. et al. Overexpression of IL-1 receptor accessory protein in stem and progenitor cells and outcome correlation in AML and MDS. *Blood* 120, 1290-1298 (2012).
7. Askmyr, M. et al. Selective killing of candidate AML stem cells by antibody targeting of IL1RAP. *Blood* 121, 3709-3713 (2013).
8. Smallridge, R. C. et al. RNA sequencing identifies multiple fusion transcripts, differentially expressed genes, and reduced expression of immune function genes in BRAF (V600E) mutant vs BRAF wild-type papillary thyroid carcinoma. *The Journal of clinical endocrinology and metabolism* 99, E338-347 (2014).
9. Greenfeder, S. A. et al. Molecular Cloning and Characterization of a Second Subunit of the Interleukin 1 Receptor Complex. *Journal of Biological Chemistry* 270, 13757-13765 (1995).
10. Lang, D. et al. The type II IL-1 receptor interacts with the IL-1 receptor accessory protein: a. *J Immunol* 161, 6871-6877 (1998).
11. Ali, S. et al. IL-1 receptor accessory protein is essential for IL-33-induced activation of T lymphocytes and mast cells. *Proc Natl Acad Sci USA* 104, 18660-18665 (2007).
12. Chackerian, A. A. et al. IL-1 receptor accessory protein and ST2 comprise the IL-33 receptor complex. *J Immunol* 179, 2551-2555 (2007).
13. Palmer, G. et al. The IL-1 receptor accessory protein (AcP) is required for IL-33 signaling and soluble AcP enhances the ability of soluble ST2 to inhibit IL-33. *Cytokine* 42, 358-364 (2008).
14. Towne, J. E., Garka, K. E., Renshaw, B. R., Virca, G. D. & Sims, J. E. Interleukin (IL)-1F6, IL-1F8, and IL-1F9 Signal through IL-1Rrp2 and IL-1RAcP to Activate the Pathway Leading to NF-κB and MAPKs. *Journal of Biological Chemistry* 279, 13677-13688 (2004).
15. Drube, S. et al. The receptor tyrosine kinase c-Kit controls IL-33 receptor signaling in mast cells. *Blood* 115, 3899-3906 (2010).
16. Ruhul Amin, A. R. et al. A role for SHPS-1/SIRPalpha1 in IL-1beta- and TNFalpha-dependent signaling. *Oncogene* 21, 8871-8878 (2002).
17. Cullinan, E. B. et al. IL-1 receptor accessory protein is an essential component of the IL-1 receptor. *J Immunol* 161, 5614-5620 (1998).

18. Braddock, M. & Quinn, A. Targeting IL-1 in inflammatory disease: new opportunities for therapeutic intervention. *Nature reviews. Drug discovery* 3, 330-339 (2004).
19. Thomas, C., Bazan, J. F. & Garcia, K. C. Structure of the activating IL-1 receptor signaling complex. *Nature structural & molecular biology* 19, 455-457 (2012).
20. Wang, D. et al. Structural insights into the assembly and activation of IL-1beta with its receptors. *Nat Immunol* 11, 905-911 (2010).
21. Bernstein, F. C. et al. The Protein Data Bank: a computer-based archival file for macromolecular structures. *Journal of molecular biology* 112, 535-542 (1977).
22. Russell, R. B. & Barton, G. J. Multiple protein sequence alignment from tertiary structure comparison: assignment of global and residue confidence levels. *Proteins* 14, 309-323 (1992).
23. Humphrey, W., Dalke, A. & Schulten, K. VMD: visual molecular dynamics. *Journal of molecular graphics* 14, 33-38, 27-38 (1996).
24. Yeung, Y. G. & Stanley, E. R. A solution for stripping antibodies from polyvinylidene fluoride immunoblots for multiple reprobing. *Analytical biochemistry* 389, 89-91 (2009).
25. Arman, A. & Auron, P. Interleukin 1 (IL-1) Induces the Activation of Stat3, in *Tissue Engineering, Stem Cells, and Gene Therapies*, Vol. 534. (ed. Y. M. Elvin) 297-307 (Springer US, 2003).
26. Onai, N., Obata-Onai, A., Tussiwand, R., Lanzavecchia, A. & Manz, M. G. Activation of the Flt3 signal transduction cascade rescues and enhances type I interferon producing and dendritic cell development. *The Journal of Experimental Medicine* 203, 227-238 (2006).
27. Larkin, M. A. et al. Clustal W and Clustal X version 2.0. *Bioinformatics* 23, 2947-2948 (2007).
28. Goujon, M. et al. A new bioinformatics analysis tools framework at EMBL-EBI. *Nucleic Acids Res* 38, W695-699 (2010).

What is claimed is:

1. A method of treating a disease or condition in a subject, to inhibit interleukin 1 receptor accessory protein (IL1RAP) interaction with interleukin 1 receptor 1 (IL1R1) or interleukin 1 receptor 2 (IL1R2), the method comprising administering to the subject an agent comprising a peptide in an amount effective to inhibit IL1RAP interaction with IL1R1 or IL1R2, wherein the peptide has 18-30 amino acids and comprises the amino acid sequence set forth in SEQ ID NO:1, SEQ ID NO:2, SEQ ID NO:6 or SEQ ID NO:7, wherein the disease or condition is chronic myeloid leukemia (CML), acute myeloid leukemia (AML), myelodysplastic syndrome (MDS), asthma, allergy, anaphylaxis, cardiovascular disease, or arthritis.

2. The method of claim 1, wherein the peptide consists of the amino acid sequence set forth in SEQ ID NO: 1 or SEQ ID NO:2.

3. The method of claim 1, wherein the peptide is a synthetic peptide.

4. The method of claim 1, wherein the peptide is conjugated to a cytotoxic agent, a polyethylene glycol (PEG) or a nanoparticle.

* * * * *